United States Patent [19]
Hobbs et al.

[11] Patent Number: 5,638,176
[45] Date of Patent: Jun. 10, 1997

[54] INEXPENSIVE INTERFEROMETRIC EYE TRACKING SYSTEM

[75] Inventors: Philip C. D. Hobbs, Briarcliff Manor; Theodore G. van Kessel, Millbrook, both of N.Y.

[73] Assignee: International Business Machines Corporation, Armonk, N.Y.

[21] Appl. No.: 670,046

[22] Filed: Jun. 25, 1996

[51] Int. Cl.⁶ ............................ G01B 9/02
[52] U.S. Cl. ............ 356/355; 356/359; 356/345; 356/349
[58] Field of Search ............ 356/345, 355, 356/357, 359, 349; 351/212

[56] References Cited

U.S. PATENT DOCUMENTS 4,660,980  4/1987  Takabayashi et al. ............ 356/357
5,513,533  5/1996  Wheeler et al. ............ 356/355
5,521,657  5/1996  Klopotek ............ 356/212
5,579,112  11/1996  Sugiyama et al. ............ 356/345

*Primary Examiner*—Frank G. Font
*Assistant Examiner*—Robert Kim
*Attorney, Agent, or Firm*—Whitham, Curtis, Whitham & McGinn; Stephen C. Kaufman, Esq.

[57]  ABSTRACT

An inexpensive eye tracking system requires no head gear. The eye tracking system uses the interference fringes between the corneal glint and the "red eye" retinal reflection to obtain an angularly resolved, background-immune eye point signal for use as a pointing device for personal computers. Tunable (eye safe) diode laser spectroscopy is used to measure the period and amplitude of the Fabry-Perot fringes caused by the interference between the corneal glint and the "red" reflection form the retina.

10 Claims, 8 Drawing Sheets

INEXPENSIVE INTERFEROMETRIC EYE TRACKING SYSTEM

BACKGROUND OF THE INVENTION

1. Field of the Invention

The present invention generally relates to eye tracking systems for a variety of systems, including human computer interfaces, and more particularly to an inexpensive interferometric eye tracking system.

2. Background Description

Human-computer interactions pose some of the most difficult challenges in the design of personal computer systems. The runaway success of the TrackPoint II™ pointing stick in differentiating and promoting IBM's ThinkPad™ notebook computers is well known. The success of that device was due to its novel design. Specifically, the pointing device is placed right in the home row of the keyboard so that the user needs not take his or her eyes off the screen to use the pointer. Although not as precise as a mouse or trackball for graphics applications such as drawing, the pointing stick offers effortless usability in text-based applications such as word processing, spread sheets, and databases (which is where most users spend most of their time), and in coarse-resolution graphical tasks, such as navigating the graphic user interface (GUI) shell. Particularly for mobile use, this is a very favorable tradeoff.

The success of GUIs and pointing devices in making computers easier to use has been universally acclaimed, almost to the point of obscuring the residual annoyances and inefficiencies in such an interface. For example, although GUI windows have a carefully defined Z-order (i.e., which one is logically on top of which), it is not currently possible to look around the upper window to see what is below it, not to lean forward to take a closer look (and have the magnification change automatically). Both of these actions are very important in making an on-screen "object" more like a physical object. At least as annoying as these is the shift of attention involved in moving the mouse cursor around the screen to the point the user is looking at. This operation distracts the user from his or her task, and so impeded his or her work, especially since it is repeated dozens or even hundreds of times a day. It would be tremendously valuable to have an accurate, robust eye tracking system which could quickly put the mouse cursor within a few pixels of the gaze point.

Eye tracking systems have been in low-level use for more than twenty years, but have never caught on, despite considerable amounts of work by the military and others. This discouraging history has been largely due to the non-ideal characteristics of existing eye tracking systems. Current generation eye trackers work by sensing the position of the glint from the cornea, due to a small area light source, and fall in two major groups; one using head gear, and the other, video equipment.

Eye trackers based on head gear generally use a light source, such as a light emitting diode (LED), and a position-sensing detector such as a lateral-effect photo diode to measure the direction of the corneal glint with respect to the head gear. Other methods, such as triangulation based on magnetic direction sensors, are needed to obtain the orientation and position of the head gear with respect to the computer screen, in order to determine the gaze point. Systems used in physiological research usually clamp the subject's head into a table-mounted fixture. Even in the computer game field, the market for such a system would probably be rather limited.

The other class of systems, those using cameras rather than headgear, typically use a charge coupled device (CCD) camera/frame grabber combination to acquire an image of the subject's head, with the corneal glint showing. This sort of system overcomes the inconvenience and discomfort of the headgear-based systems, but at a price in cost and accuracy. Extensive image processing is required to locate the subject's face and nose in the camera's field of view, following which further processing can recover the position of the corneal glint with respect to the nose, and hence the direction of gaze. This procedure is complex, since the motion of the corneal glint is very small (a few millimeters) and the motion of the subject's head is many times larger, so that the precision obtained with cameras of reasonable cost is quite low, in spite of the expensive equipment required. In addition, such systems have great difficulty with people having hooded eyes or wearing eye glasses.

SUMMARY OF THE INVENTION

It is therefore an object of the present invention to provide an inexpensive eye tracking system which requires no head gear and yet provides an accurate and precision tracking system.

It is another object of the invention to provide an eye tracking system which is simple and can be used in a variety of applications including an improved human computer interface.

According to the invention, there is provided an eye tracking system that uses the interference fringes between the corneal glint and the "red eye" retinal reflection to obtain an angularly resolved, background-immune eye point signal for use as for example a pointing device for personal computers. Tunable (eye safe) diode laser spectroscopy is used to measure the period and amplitude of the Fabry-Perot fringes caused by the interference between the corneal glint and the "red" reflection from the retina.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
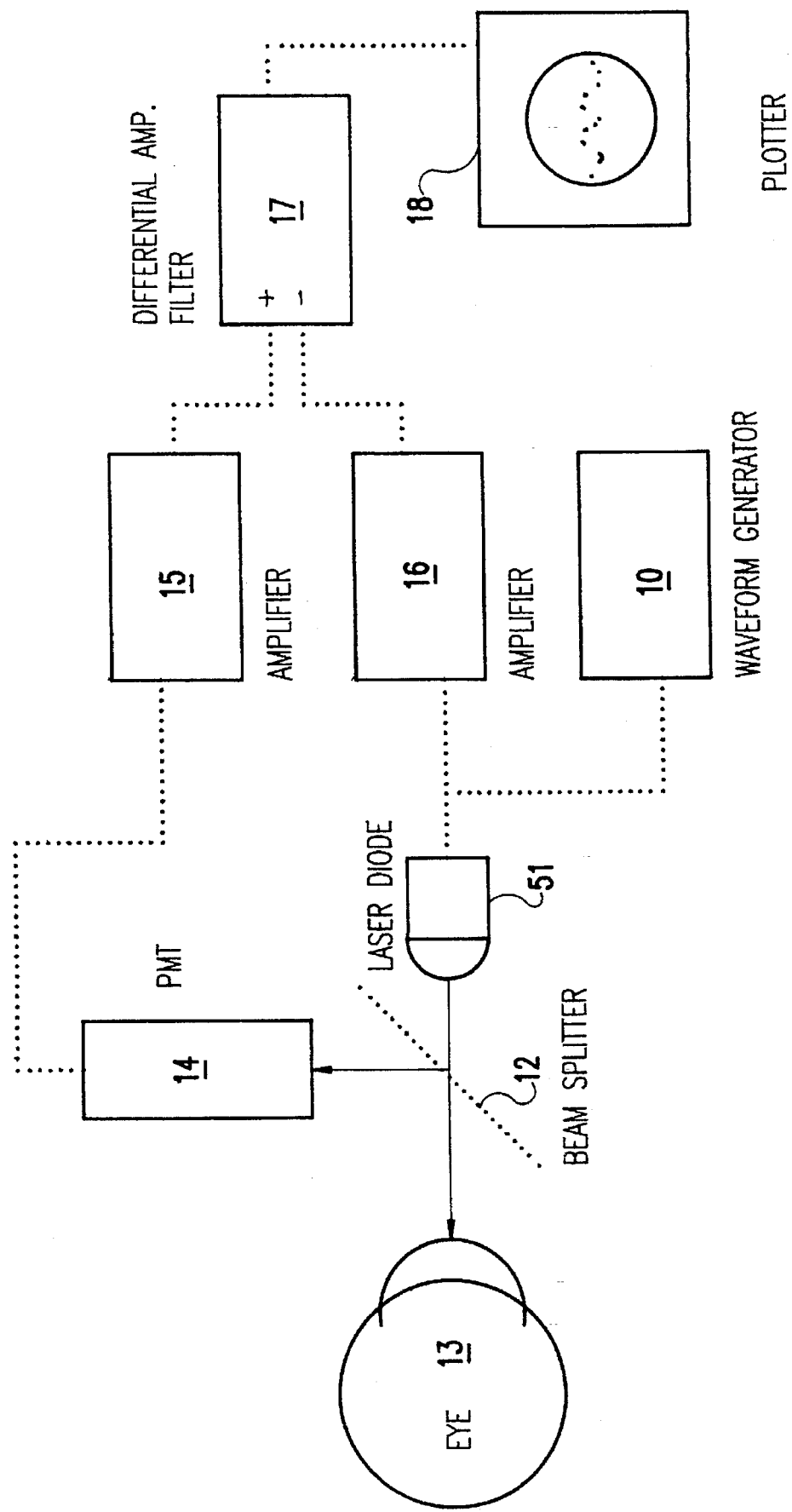
FIG. 1 is a block diagram of a test set up to measure the dark field interference.
Figure 2:
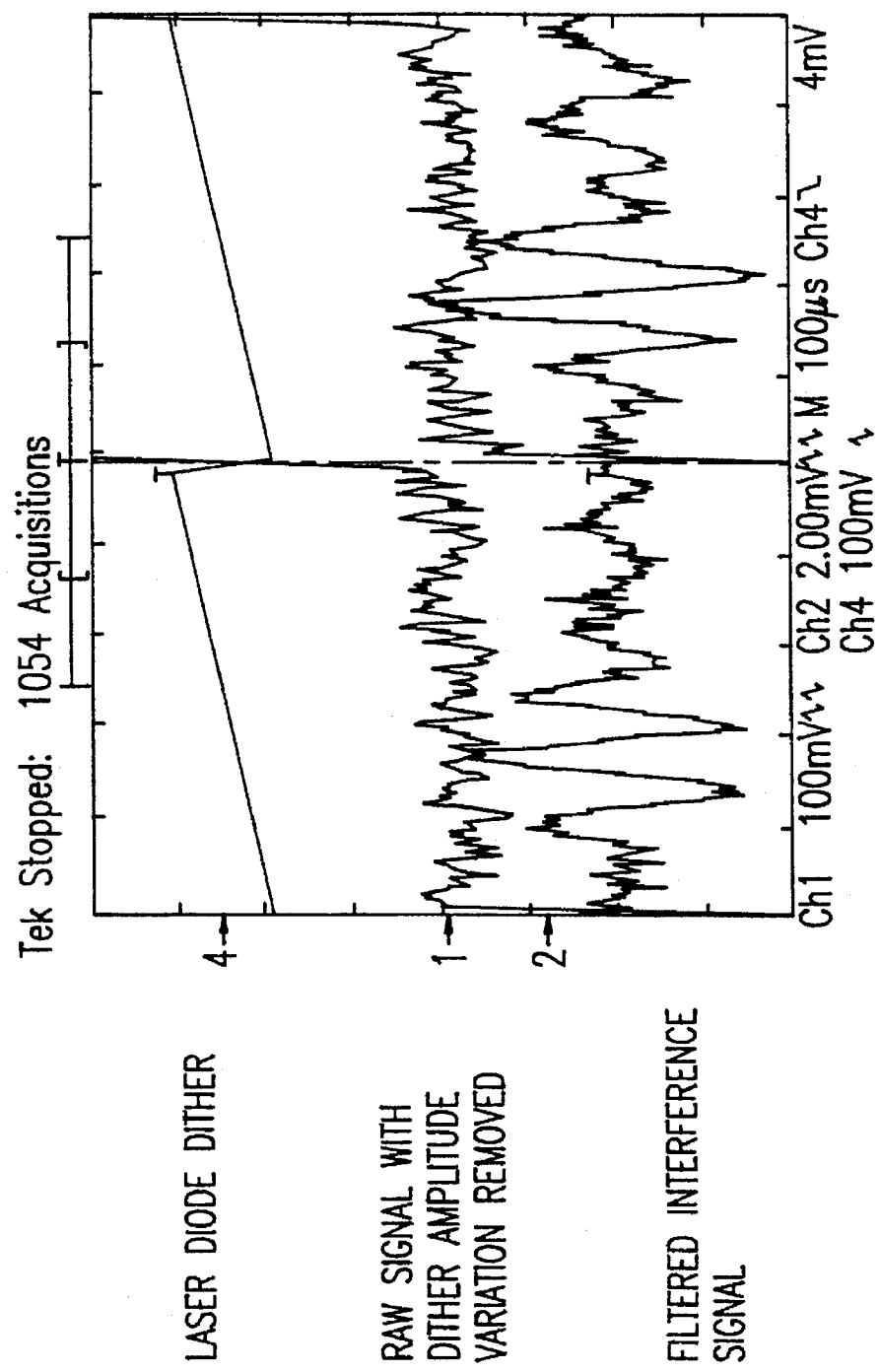
FIG. 2 is a graph showing the interference pattern of the eye.
Figure 3:
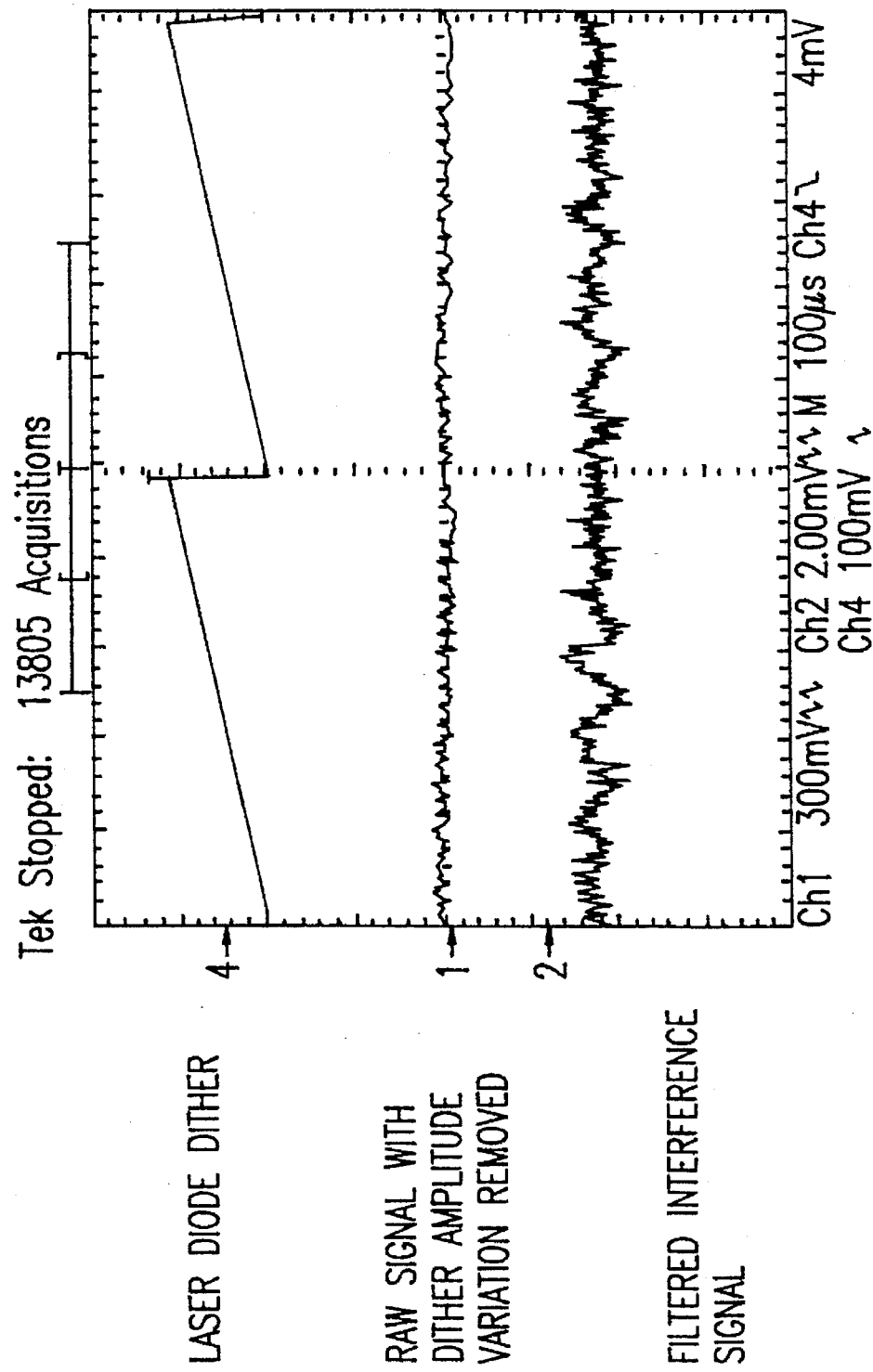
FIG. 3 is a graph showing the interference pattern of a 20 mm lens.
Figure 4:
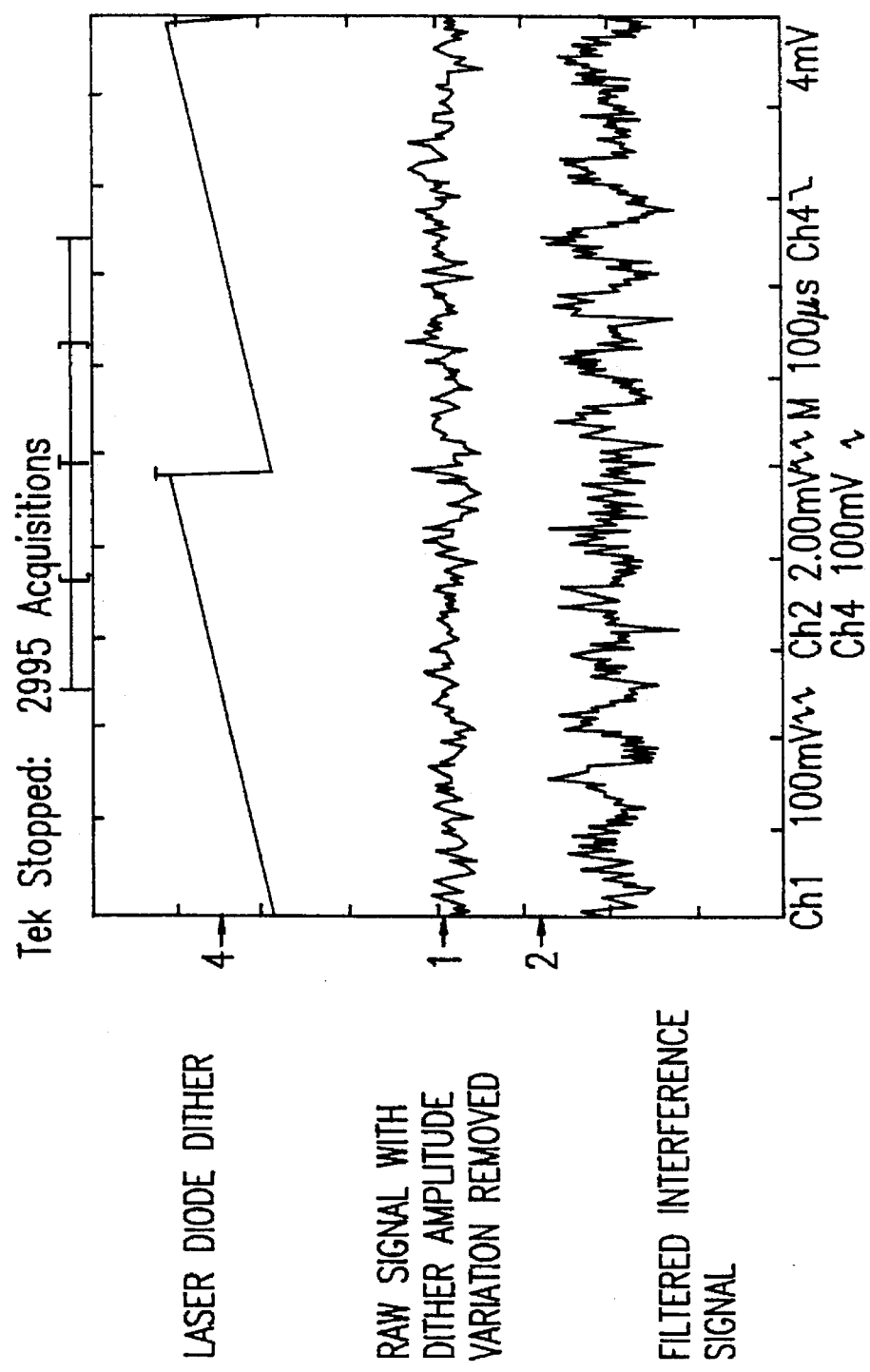
FIG. 4 is a graph showing the interference pattern of white shirt fabric.
Figure 5:
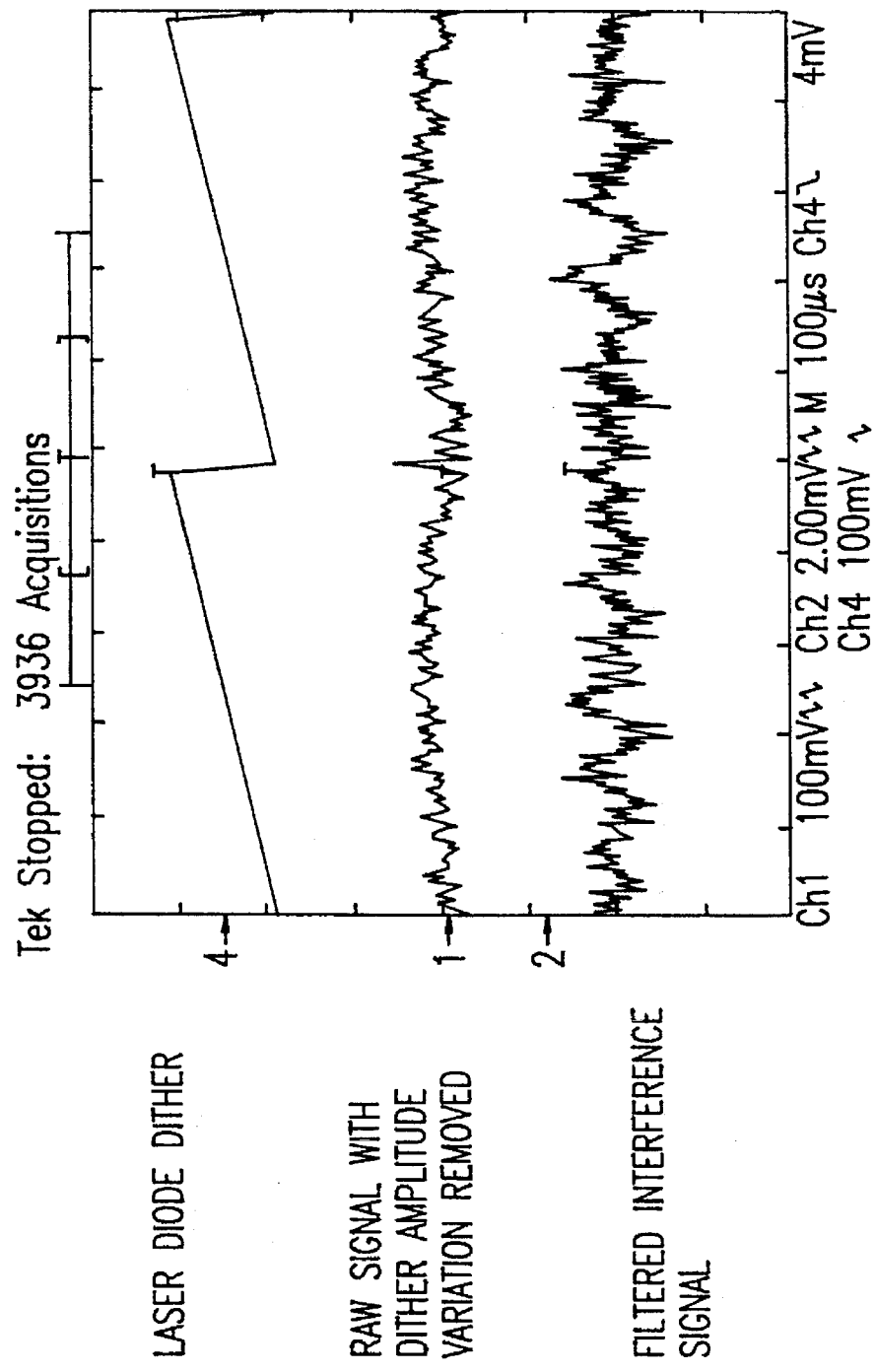
FIG. 5 is a graph showing the interference pattern of white paper.
Figure 6:
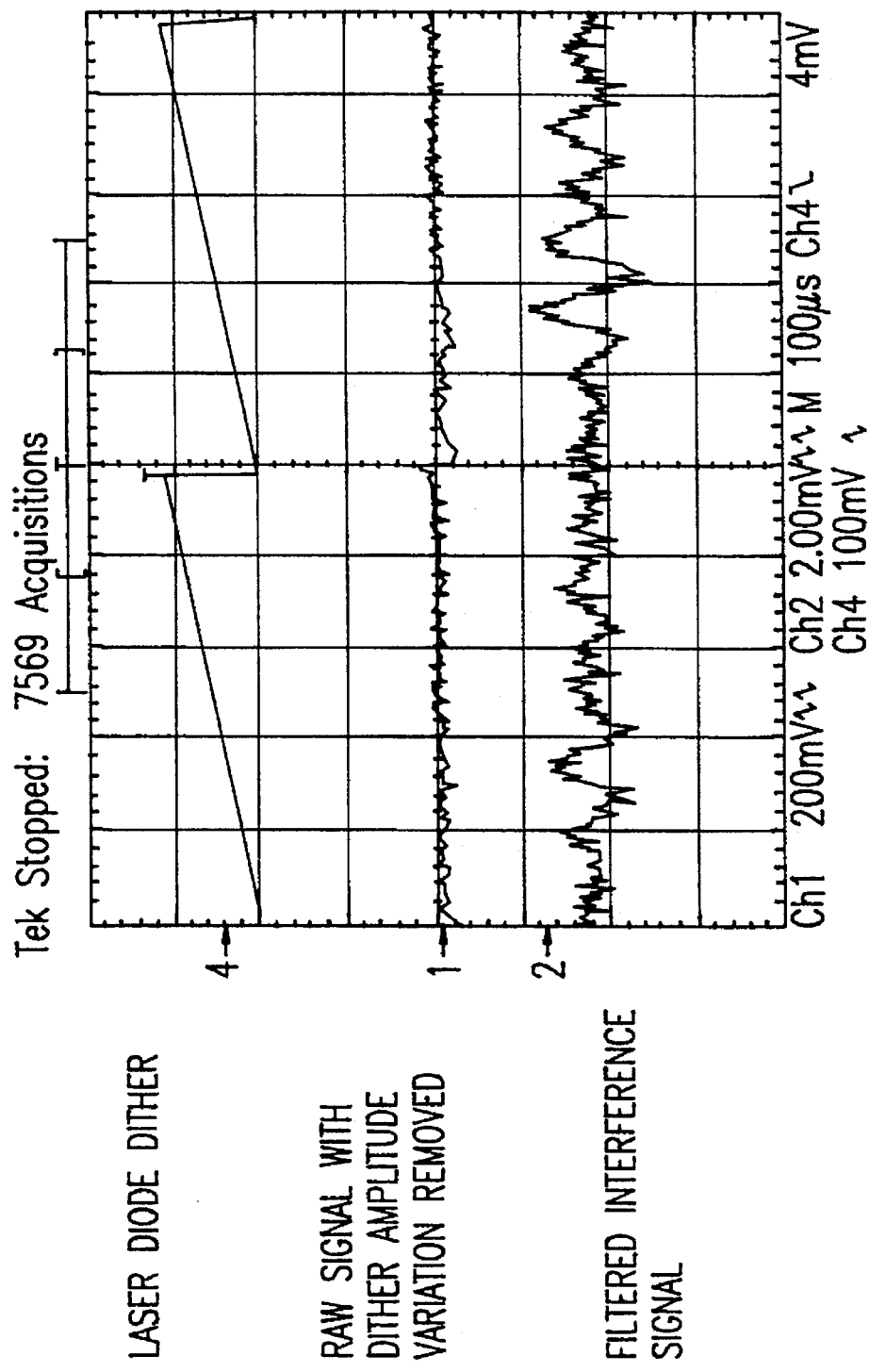
FIG. 6 is a graph showing the interference pattern of a subject's face.

All amateur photographers are familiar with the "red eye" reflection from people's eyes produced by the camera's flash unit. This phenomena is caused by the strong scattering of light from the retina itself, and because the retina is in focus, the scattered light tends to return along the same direction from which it came. If the flash unit is too close to the camera lens, a considerable amount of the retro reflected light will enter the lens, resulting in a bright red disc on the photograph. From a viewpoint close to the flash unit (as in compact cameras), the apparent surface brightness of the red eye reflection is comparable to the reflection form skin and clothing. The red eye reflection contains angular information about the gaze point, since if the source and detector are reasonably far apart (a few degrees), a red eye signal is only seen if the gaze point is between them, and its strength depends on the position of the gaze point. Two or three such sensors could in principle determine the gaze point.

Unfortunately, the effect in itself is not sufficient to make a practical sensor. Depending on the room arrangement and the user's preferences, the user's head could be located anywhere from 40 to 200 cm from the screen, and perhaps ±20° in angle. A non-imaging sensor will have to receive light from this entire area, and the red eye reflection is not bright enough to be distinguishable in an imaging measurement from the background of room light, light from the monitor, and reflections of the sensor's own light from the user's face, clothing, walls, and furniture. One way to make the light reflected from the retina distinguishable is to force it to be at a different baseband frequency from the other sources.

By modulating the sensor's light source, it is possible to reject the room lights and the display's light, but this strategy is powerless by itself to adequately reject the facial and clothing reflections in the detector's field of view, since there unwanted signals will share the source's modulation characteristics. The eye differs from these unwanted scatterers in one vital and unique respect, however. It has two scattering surfaces, the cornea and the retina, which are separated by a transparent medium (the cornea, lens, and humors of the eye). Thus, the two signals can be optically superposed, so that they interfere.

If the sensor's light source were broadband, so that the interference washed out, or fixed-tuned, so that no fringes could be observed, this fact would be of little use; however, by using a tunable, narrow band source, such as a single longitudinal mode diode laser, clear interference fringes can be observed. Such sources are now plentiful and inexpensive, and they can easily be operated so as to satisfy by a wide margin the Occupational Safety and Health Administration (OSHA) regulations for long term (eight hours per day) intra-ocular exposure to laser radiation (about 200 μW continuous wave at 840 nm).

The human eye has properties which make it well suited to a tunable diode laser spectroscopic measurement. It can sustain reasonable laser powers without damage, and it has an optical path difference of about 6 cm round trip, so that a typical cleared-cavity diode laser's current tuning range of 1–2 $cm^{-2}$ spans several cycles of the fringe period. If the laser is tuned rapidly, say 1 $cm^{-1}$ in 50 μs (10 kHz repetition rate), the resulting signal will come in at around 60 kHz, which is conveniently above the worst of the background noise. The shot noise of the background is of course white in character and is not diminished by this strategy. Fortunately, nothing else in a typical room exhibits this range of path length differences. Windows are farther away, and are much thinner, so they are not much of a problem, and other transparent objects are typically planar specular reflectors, so that their reflections should not normally reach the detector. Any reflection fortuitously reaching a detector can be accounted for by diversity techniques.

The preferred embodiment of the invention uses ordinary bright-field detection, as this is sufficient for most environments. An interferometric detection system similar to that disclosed in U.S. Pat. No. 5,192,870 to Hobbs can be used to improve the signal to noise ratio (SNR) and to reject room lights and scatter from surfaces out of the field of view.

If an interferometric detector is used, then through temporal-coherence control strategies such as those commonly used in optical coherence domain reflectometry, it is possible to tailor the range of sensor-eye distances within which a detectable interference signal will be received by the detectors. These strategies involve frequency-modulating the diode laser by varying its injection current with a waveform so chosen that the time autocorrlation of the light has one or more peaks, surrounded by areas of very low autocorrelation amplitude. An example is sinusoidal modulation at a frequency $f_{mod}$, which gives rise to autocorrelation peaks spaced by $c/2f_{mod}$ in range, corresponding to round-trip delays of integer multiples of one period of the modulation. Although there are sharp mathematical limits on the behavior of autocorrelation functions (e.g., their Fourier transforms are purely real), and the amplitude and frequency of the diode laser cannot be varied independently using purely injection current modulation, enough control can be exerted on the temporal coherence of the beam that problems due to spurious reflections and to signals from the eyes of people farther away can be practically eliminated in this fashion.

The signal processing necessary for this system is easily within the capabilities of a cheap ($5) commodity digital signal processing (DSP) chip such as the TMS320C10 with less than 256 kB of memory and a very simple data acquisition front end. It is much simpler than that required for the video-based strategies.

Referring to the drawings, and more particularly to FIG. 1, there is shown a dark field interference detection apparatus used to measure interference patterns. A waveform generator 10 modulates a tunable laser diode 11. The modulated light output of the laser diode 11 is passed by a beam splitter 11 to a subject's eye 13. The reflected image from the subject's eye 13 is reflected by the beam splitter 12 to the photo multiplier tube (PMT) 14, the output of which is amplified by amplifier 15. The output of waveform generator 10 is also amplified by amplifier 16. The outputs of amplifiers 15 and 16 are supplied to a differential amplifier and filter 17, the output of which is plotted by a plotter 18. The plotter 18 may be an oscilloscope or pen plotter.

The graphs shown in FIGS. 2 to 6 show the interference fringes clearly, and the ease of distinguishing an eye reflection form one from skin or clothing. The signal to noise ratio shown is unrealistically poor, since the filtering operation used took no advantage of the periodic nature of the excitation, did not reject the harmonic content of the excitation light at the measurement frequency, and did not adjust the peak frequency deviation to concentrate all the energy into one specific harmonic of the scan frequency.

These measurements were taken in darkness, using a simple bright field detector, so that they do not represent a practical device. FIG. 7 shows a practical implementation of the invention. This implementation includes a diode laser 71 which is modulated by modulator 72 receiving as its input a sawtooth modulating signal from sawtooth generator 73. The laser beam emitted by the laser 71 passes through lens 74 which transforms it into a narrow beam whose divergence angle is sufficiently small for it to pass through the remainder of the optical system. Optionally, the lens 74 may be a collimating lens. The narrow beam is scanned in one dimension by a rotating polygon mirror 75. The beam reflected from the rotating polygon mirror 75 passes through beam forming optics 76 to the subject's eye 77. The beam forming optics 76 may be, for example, a holographic optical element followed by a large Fresnel lens which produces a shaped beam whose far-field intensity pattern includes two orthogonal line segments. The light reflected from the subject's eye 77 passes back through the beam forming optics 76 and is again reflected by the rotating polygon mirror 75 through a baffle 78 to a photo detector 79. The output of the photo detector is an A.C. signal, corresponding to the sawtooth modulation of the original laser beam. This detected A.C. signal is input to signal processing circuits 80 which determine, by statistical model, an estimate of where the subject is looking.

Figure 7A:
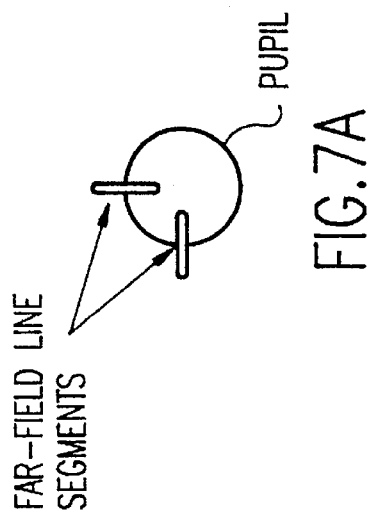
FIG. 7A illustrates the far-field line segments formed by the beam former in the apparatus shown in FIG. 7.
Figure 7:
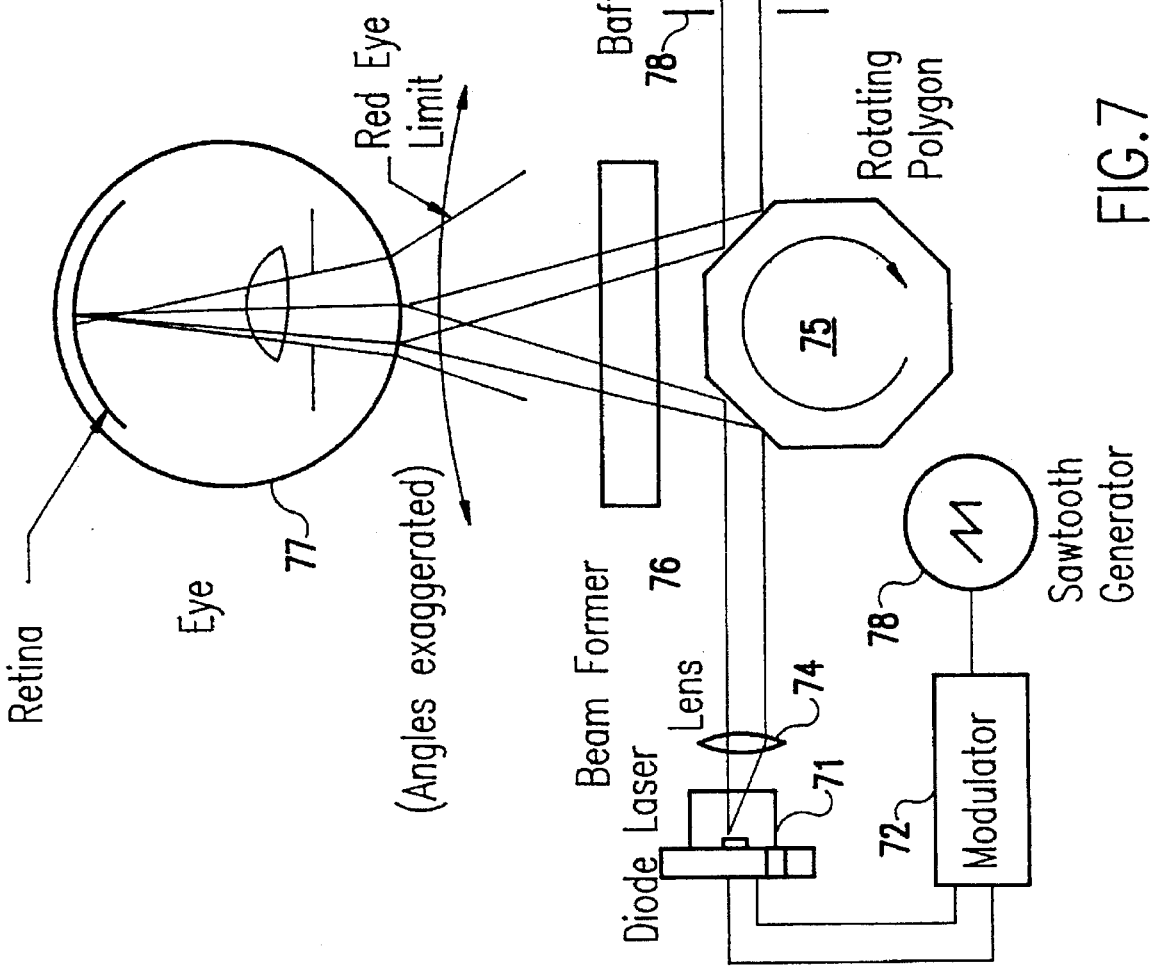
FIG. 7 is a block diagram of a preferred embodiment of the eye tracking apparatus according to the invention.

The far-field line segments from beam forming optics 75 are shown in FIG. 7A imaged on the subject's eye. Note that these line segments need not intersect. The dimensions of the line segments are chosen so that in the angular range and spatial domain of interest, during at least part of the scan period, the reflection of the shaped beam from the cornea of the subject's eye, as seen from at least two of the detectors, are so positioned that they cross the edges of the pupil of the subject's eye.

In the preferred embodiment of the invention, detector 79 is descanned, i.e., the laser light returning from the illuminated region is reflected from the scanning mirror 75 again, to make the apparent position of the illuminated region stationary as viewed from detector 79. Because of the limited size of the rotating polygon 75, it is not possible to get a sufficient range of detector angles from this arrangement, so that two or more sensors of the type shown in FIG. 7 must be disposed so as to view the eye from different angles. With relaxed operating conditions (e.g., forbidding direct sunlight, or with the use of very narrow-band optical filters), it may be possible to use a staring detector (i.e., one which receives light from its whole field of view, all the time). With staring detectors, multiple sources are unnecessary, so one source and scanner will suffice.

The "red-eye" reflection from the rear (retina) of the subject's eye illuminates the pupil from behind, so that the optical interference between the corneal glint and the red-eye can occur only in the area common to both the glint and red-eye, i.e., their overlap, as shown in FIG. 7. As the angle of the subject's eye changes with respect to the sensor changes, the area of overlap will change as well, so that the strength of the A.C. detected signals at the detectors will be functions of the angles between radial lines joining the center of the pupil to the sensors and the line of sight (LOS) or gaze line. The two line segments in the far-field pattern (FIG. 7A) help to make the functional dependence of the strength of the A.C. interference simpler, by approximately decoupling the vertical and horizontal axes. Knowledge of these angles is sufficient to determine both the eye position and the line of sight, so the differences in these A.C. signal strengths are translated by a statistical model into estimates of where the subject is looking.

Figure 8:
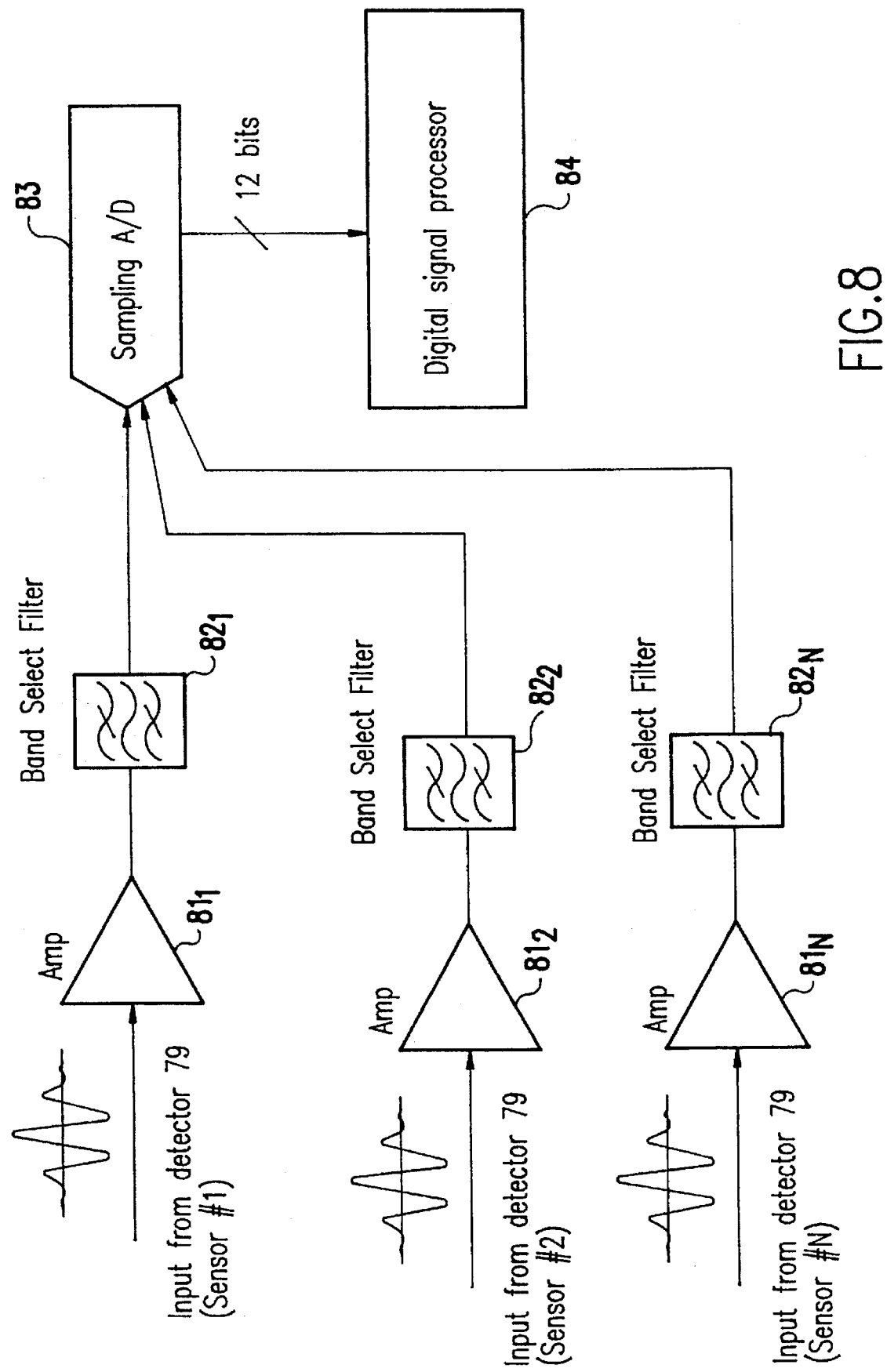
FIG. 8 is a block diagram of the signal processing circuitry of the apparatus shown in FIG. 7.

The signal received from the detector 79 in each sensor goes to the signal processing system 80. A block diagram of the signal processing subsystem is shown in FIG. 8. The photo currents from detector 79 sensors (1 through N) are converted to voltages by amplifiers $81_1$ to $81_N$ and then filtered by filters $82_1$ to $82_N$ which remove out-of-band noise components and prevents aliasing. The signals from filters $82_1$ to $82_N$ are then digitized by A/D converter 83, and the resulting digital data stream is sent to a digital signal processor (DSP) 84.

The DSP 84 performs short term power spectrum estimation to extract time-resolved estimates of the strength of the signal at each harmonic of the modulation frequency in each sensor. When the scanned beam crosses the pupil of the user's eye, a burst in the intensity of the fifth through seventh harmonics will be registered. As long as the positions of the detectors and the radius of curvature $r_{curve}$ of the user's cornea are known, the envelope heights of the bursts are functions of head position and of the gaze point. Provided that the distance from the sensors to the head is of the same order of magnitude as the distance between sensors and much greater than $r_{curve}$ and the sensors lie in or near the plane of interest, the burst envelope heights are strong functions of gaze point and weak functions of head position. By comparing the envelope heights of the bursts from the different detectors, the gaze point of the eye can be obtained. By adjusting the amplitude of the sawtooth modulation so that the fringes pass through nearly an integral number of cycles (say N=6), the filter at $Nf_{mod}$ will get most of the energy, which will improve the signal to noise ratio of the measurement.

While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. An eye tracking system comprising:

a narrow band tunable light source;

modulating means for modulating said light source with a modulating frequency $f_{mod}$;

a photo detector;

scanning means passing modulated light from said light source to a user's eye and reflecting light returned from a cornea and a retina of the user's eye to said photo detector, said photo detector measuring interference fringes formed by light returned from the cornea and light returned by the retina; and signal processing means connected to said photo detector for processing the measured interference fringes between light returned from the cornea and the retina of the eye to generate an output signal representative of a direction of a user's gaze.

2. The eye tracking system recited in claim 1 wherein said signal processing means comprises:

an amplifier for converting a current signal from said photo detector to voltage signal;

a filter for removing out-of-band noise components from the voltage signal;

an analog-to-digital converter for sampling the filtered voltage signal and generating a digital data stream; and a digital signal processor receiving said digital data stream and performing short-term power spectrum estimation to extract time-resolved estimates of signal strength at each harmonic of the modulation frequency.

3. The eye tracking system recited in claim 2 wherein said photo detector comprises a plurality of sensors disposed so as to view the eye from different angles, said signal processing means including a separate amplifier and filter for each of said plurality of sensors and said analog-to-digital converter sampling filtered voltage signals from each of the filters, strengths of detected signals at said plurality of sensors being functions of angles between radial lines joining a center of a pupil of the user's eye to the sensors and a line of sight corresponding to a user's gaze.

4. The eye tracking system recited in claim 3 wherein said scanning means includes optical beam forming means which produces a shaped beam whose far-field intensity pattern includes two orthogonal line segments, dimensions of said line segments being chosen so that during at least a part of a scan period, a reflection of the shaped beam from the cornea of the eye as seen from at least two of said plurality of sensors are so positioned that the line segments cross edges of the pupil of the eye.

5. The eye tracking system recited in claim 4 wherein said scanning means further includes a rotating polygon mirror for reflecting and scanning modulated light from said light source through said optical beam forming means to the eye and reflecting and descanning light from the eye to the photo detector.

6. The eye tracking system recited in claim 2 wherein the narrowband tunable light source is a diode laser and said modulating means comprises a modulator receiving a predetermined modulating frequency which provides autocorrelation peaks spaced in range, corresponding to round-trip delays of integer multiples of one period of the modulation.

7. A method of tracking a user's eye comprising the steps of:

modulating a tunable light source with a modulation frequency $f_{mod}$ to produce a modulated light beam;

scanning the modulated light beam across the user's eye;

measuring interference fringes formed by light returned from a cornea and light returned from a retina of the user's eye; and processing the measured interference fringes between light returned from the cornea and the retina of the eye to generate an output signal representative of a direction of a user's gaze.

8. The method of tracking a user's eye recited in claim 7 wherein the step of measuring is performed using a plurality of sensors, the step of processing including the step of detecting strengths of detected signals at said plurality of sensors, the strengths of the detected signals being functions of angles between radial lines joining a center of a pupil of the user's eye to the sensors and a line of sight corresponding to a user's gaze.

9. The method of tracking a user's eye recited in claim 8 further including the step of forming a shaped beam of the modulated and scanned light beam wherein a far-field intensity pattern of the shaped beam includes two orthogonal line segments, dimensions of said line segments being chosen so that during at least a part of a scan period, a reflection of the shaped beam from the cornea of the eye as seen from at least two of said plurality of sensors are so positioned that the line segments cross edges of the pupil of the eye.

10. The method of tracking a user's eye recited in claim 7 wherein the step of modulating is performed with a modulating frequency which provides autocorrelation peaks spaced in range, corresponding to round-trip delays of integer multiples of one period of the modulation.

* * * * *